(12) United States Patent
Ochiya et al.

(10) Patent No.: US 8,921,333 B2
(45) Date of Patent: Dec. 30, 2014

(54) THERAPEUTIC AGENT FOR TUMOR

(75) Inventors: Takahiro Ochiya, Tokyo (JP); Ryou-u Takahashi, Tokyo (JP)

(73) Assignees: National Cancer Center, Tokyo (JP); Asahi Pharma Corporation, Tokyo (JP)

( * ) Notice: Subject to any disclaimer, the term of this patent is extended or adjusted under 35 U.S.C. 154(b) by 18 days.

(21) Appl. No.: 13/498,771

(22) PCT Filed: Oct. 1, 2010

(86) PCT No.: PCT/JP2010/067288
§ 371 (c)(1),
(2), (4) Date: Mar. 28, 2012

(87) PCT Pub. No.: WO2011/040613
PCT Pub. Date: Apr. 7, 2011

(65) Prior Publication Data
US 2012/0252881 A1 Oct. 4, 2012

(30) Foreign Application Priority Data

Oct. 1, 2009 (JP) ................................. 2009-230016

(51) Int. Cl.
| | | |
|---|---|---|
| A61K 48/00 | (2006.01) | |
| A61K 31/7088 | (2006.01) | |
| A61K 31/713 | (2006.01) | |
| C12N 15/113 | (2010.01) | |
| C12Q 1/68 | (2006.01) | |

(52) U.S. Cl.
CPC ........... *A61K 31/7088* (2013.01); *A61K 31/713* (2013.01); *C12N 15/113* (2013.01); *C12Q 1/6886* (2013.01); *C12N 2310/141* (2013.01); *C12N 2330/10* (2013.01); *C12Q 2600/106* (2013.01); *C12Q 2600/136* (2013.01); *C12Q 2600/178* (2013.01)
USPC ............................ 514/44; 536/24.5; 536/24.1

(58) Field of Classification Search
None
See application file for complete search history.

(56) References Cited

U.S. PATENT DOCUMENTS

| | | | |
|---|---|---|---|
| 7,723,035 B2 | 5/2010 | Croce et al. | |
| 7,825,229 B2 * | 11/2010 | Itzhak et al. | ........... 536/23.1 |
| 2004/0152112 A1 | 8/2004 | Croce et al. | |
| 2006/0105360 A1 | 5/2006 | Croce et al. | |
| 2006/0165659 A1 | 7/2006 | Croce et al. | |
| 2008/0306017 A1 | 12/2008 | Croce et al. | |
| 2009/0123533 A1 | 5/2009 | Croce et al. | |
| 2009/0186353 A1* | 7/2009 | Aharonov et al. | ............ 435/6 |
| 2009/0202624 A1 | 8/2009 | Inazawa et al. | |
| 2010/0088775 A1 | 4/2010 | Khew-Goodall et al. | |
| 2010/0173319 A1 | 7/2010 | Croce et al. | |
| 2010/0179213 A1 | 7/2010 | Patrawala et al. | |
| 2011/0177968 A1 | 7/2011 | Croce et al. | |
| 2011/0190160 A1 | 8/2011 | Croce et al. | |

FOREIGN PATENT DOCUMENTS

| | | |
|---|---|---|
| EP | 2 199 412 A1 | 6/2010 |
| JP | 2006-506469 A | 2/2006 |
| JP | 2008-86201 A | 4/2008 |
| JP | 2009-171876 A | 8/2009 |
| JP | 2009-531018 A | 9/2009 |
| WO | 2005/078139 | 8/2005 |
| WO | 2007/081720 A2 | 7/2007 |
| WO | 2007/137342 A1 | 12/2007 |
| WO | 2008/112283 A2 | 9/2008 |
| WO | 2009/075787 A1 | 6/2009 |
| WO | 2009/080437 A1 | 7/2009 |
| WO | 2010/056737 A2 | 5/2010 |
| WO | 2010/066384 A1 | 6/2010 |

OTHER PUBLICATIONS

Extended European Search Report for European Patent Appl. No. 10820727.5, dated Mar. 4, 2013.
Erik A.C. Wiemer, "The role of microRNAs in cancer: No small matter" *European Journal of Cancer*, vol. 43, No. 10, pp. 1529-1544, 2007.
Sayda M. Elbashir et al., "Duplexes of 21-nucleotide RNAs mediate RNA interference in cultured mammalian cells", Nature, vol. 411, May 24, 2001, pp. 494-498.
Chang-Zheng Chen et al., "MicroRNAs Modulate Hematopoietic Lineage Differentiation", Science, vol. 303, Jan. 2, 2004, pp. 83-86.
Kimi Honma et al., "RPN2 gene confers docetaxel resistance in breast cancerr", Nature Medicine, vol. 14, No. 9, Sep. 2008, pp. 939-948.
Hideki Masaki et al., "Cancer Stem Cell Based Drug Discovery", Experimental Medicine, vol. 26, No. 8, May, 2008, pp. 1232-1238.
Yanfang Wang et al., "ST14 (Suppression of Tumorigenicity 14) Gene is a Target for miR-27b, and the Inhibitory Effect of ST14 on Cell Growth is Independent of miR-27b Regulation.", Journal of Biological Chemistry, vol. 284, No. 34, Aug. 21, 2009, pp. 23094-23106.
Yuki Tsuchiya et al., "MicroRNA Regulates the Expression of Human Cytochrome P450 1B1", Cancer Research, vol. 66, No. 18, Sep. 15, 2006, pp. 9090-9098.
Olga Kovalchuk et al., "Involvement of microRNA-451 in resistance of the MCF-7 breast cancer cells to chemotherapeutic drug doxorubicin", Molecular Cancer Therapeutics, vol. 7, No. 7, Jul. 2008, pp. 2152-2159.
Search report from International Application No. PCT/JP2010/067288, mail date is Oct. 26, 2010.
Office Action for JP Patent Application No. 2011-534353 mailed Jul. 8, 2014, along with an English language translation.

* cited by examiner

*Primary Examiner* — Kimberly Chong
(74) *Attorney, Agent, or Firm* — Greenblum & Bernstein, P.L.C.

(57) ABSTRACT

The present invention provides a therapeutic agent for a tumor, particularly a therapeutic agent for drug-resistant cancer, an agent for suppression or prophylaxis of tumor metastasis, and an agent for suppression or prophylaxis of cancer recurrence, containing a nucleic acid containing miR27b or a nucleotide having a nucleotide sequence having an identity of 70% or more with the nucleotide sequence shown by SEQ ID NO: 1 and having a function equivalent to miR27b.

13 Claims, 6 Drawing Sheets

THERAPEUTIC AGENT FOR TUMOR

SEQUENCE LISTING

The instant application contains a Sequence Listing which has been submitted in ASCII format via EFS-Web and is hereby incorporated by reference in its entirety. Said ASCII copy, created on Apr. 24, 2012, is named P41658.txt and is 4,975 bytes in size.

TECHNICAL FIELD

The present invention relates to a therapeutic agent for tumor, particularly a cell proliferation inhibitor for drug-resistant cancer, an agent for suppressing or preventing tumor metastasis, an agent for suppressing or preventing cancer recurrence, and the like.

BACKGROUND ART

At present, RNA interference (RNAi) technique is frequently utilized for life science researches, and usefulness thereof has been confirmed widely. RNAi refers to a phenomenon of suppression of gene expression by degradation of mRNA, which is specific to a double-stranded RNA sequence. Ever since the report in 2001 that a low molecular weight double-stranded RNA having 21 bases can mediate RNAi in a mammalian cell (non-patent document 1), siRNA (small interference RNA) has been frequently used as a method for suppressing expression of a target gene. siRNA is expected to be applicable to pharmaceutical products and treatment of various intractable diseases including cancer.

miRNA (microRNA) is an endogenous, non-coding RNA of about 20-25 bases encoded on the genome. miRNA is transcribed from an miRNA gene on the genomic DNA first as a primary transcript (Primary miRNA, hereinafter to be referred to as "Pri-miRNA") having a length of about several hundred to several thousand bases, and then processed into a pre-miRNA (precursor miRNA) having a hairpin structure of about 60-70 bases. Thereafter, it moves from the nucleus into the cytoplasm and is further processed into a double-stranded mature miRNA of about 20-25 bases. It is known that one strand of the double-stranded mature miRNA forms a complex with a protein called RISC and acts on mRNA of a target gene to inhibit translation of the target gene (see, for example, non-patent document 1).

There are 1000 or more kinds of miRNAs known for human, mouse and the like, each of which is suggested to regulate expression of plural target genes, and be involved in various biological phenomena such as growth, differentiation and the like of the cell. For example, miRNA involved in differentiation of hematopoietic cell and nerve cell, and the like has been reported (see, for example, non-patent document 2). In addition, there are reports on miRNA involved in cancer cell growth, where utilization of miRNA expression pattern for clinical cancer diagnosis, and a treatment method of cancer which suppresses cancer cell growth by suppressing expression of miRNA have been proposed (see, for example, patent documents 1 and 2).

On the other hand, it is widely known that the highest hurdle for the cancer chemotherapy is drug resistance acquired by cancer cells. As the mechanism of acquiring resistance, various theories have been proposed including increased expression of ABC transporter which is one kind of drug transporter, increased expression of RPN2 gene which is a glycosylation enzyme (non-patent document 3) and the like, and a strong ability of cancer stem cells to excrete anti-cancer agents is drawing attention in recent years (non-patent document 4).

Expression of microRNA-27b (miR27b) is observed in various cancer cells such as breast cancer cells (non-patent document 5), prostate cancer cells (patent document 3), pancreatic cancer cells (patent document 4) and the like. As for physiological function, non-patent document 5 states that forced expression of miR27b in ZR75 cell, which is a breast cancer low-metastatic cell, promotes cell proliferation. However, there is no document that has reported the relationship between miR27b and drug-resistant cancer cells.

DOCUMENT LIST

Patent Documents patent document 1: JP-A-2008-86201
patent document 2: JP-A-2006-506469
patent document 3: WO2008/112283
patent document 4: WO2009/075787

Non-Patent Documents non-patent document 1: Elbashir S M et. al. Nature 411:494-498 (2001)
non-patent document 2: Science 303: 654 83-86 (2004)
non-patent document 3: Nature Medicine 14, 939-948, 2008
non-patent document 4: Experimental Medicine, vol. 26, No. 8, 2008
non-patent document 5: J. Biol. Chem., Vol. 284, Issue 34, 23094-23106, 2009

SUMMARY OF THE INVENTION

Problems to be Solved by the Invention

An object of the present invention is to provide a therapeutic agent for tumor, particularly a therapeutic agent for drug-resistant cancer, an agent for suppression or prophylaxis of tumor metastasis, an agent for suppression or prophylaxis of cancer recurrence, a medicament utilizing the aforementioned agent, a method of determining a drug-resistant cancer, a method of determining a cancer stem cell, a method of predicting the prognosis of cancer treatment, an agent for determining a drug-resistant cancer or a cancer stem cell, a method of screening for a substance having an action to suppress growth of a drug-resistant cancer, and a method of screening for a substance having an action to inhibiting tumor metastasis.

Means of Solving the Problems

The present inventors have conducted intensive functional analysis of miR27b, and found that the expression of miR27b markedly decreases in drug-resistant cancer cells, and constitutive expression of miR27b in drug-resistant cancer cells suppresses growth of the drug-resistant cancer cells. While a cancer cell highly expressing MDR1, which is a drug efflux pump molecule, is known to be resistant to anti-cancer agents, miR27b has been newly clarified to suppress MDR1 expression.

In addition, the present inventors newly found that RPN2 expression is suppressed by introducing miR27b into cancer cells. As for RPN2, it is known that suppression of RPN2 expression results in suppression of cancer metastasis (Nat. Med. 2008 September; 14(9): 939-48).

Furthermore, while cancer stem cells are said to be resistant to general antitumor agents and deeply involved in the recurrence and metastasis of tumor, low expression level of miR27b in the cancer stem cells was clarified, and it was newly found that introduction of pre-miR27b into breast cancer stem cells leads to the suppression of CD44 expressing cell and the reduction of the ratio of the cancer stem cells.

Based on these findings, the present inventors have found (1) miR27b is useful for the treatment of drug-resistant cancer, (2) miR27b can suppress cancer metastasis by suppressing RPN2 expression, (3) miR27b is useful for cancer stem cell differentiation therapy, and (4) drug-resistant cancer and cancer stem cells can be determined using miR27b expression as an index, which resulted in the completion of the present invention.

That is, the present invention relates to the following.

[1] A therapeutic agent for a tumor, comprising a nucleic acid comprising miR27b or a nucleotide having a nucleotide sequence having an identity of 70% or more with the nucleotide sequence shown by SEQ ID NO: 1 and having a function equivalent to miR27b.
[2] The therapeutic agent of [1], wherein the nucleic acid is single stranded or double stranded.
[3] The therapeutic agent of [1], wherein the miR27b is a nucleotide consisting of the nucleotide sequence shown by SEQ ID NO: 1.
[4] The therapeutic agent of [1], wherein the nucleic acid is an RNA consisting of the nucleotide sequence shown by SEQ ID NO: 1 or a partial sequence thereof, or a modified product thereof.
[5] The therapeutic agent of [1], wherein the nucleic acid is an RNA consisting of the nucleotide sequence shown by SEQ ID NO: 1 or a modified product thereof.
[6] The therapeutic agent of [1], wherein the nucleic acid comprising miR27b is at least one kind of nucleic acid selected from the group consisting of miR27b and a precursor thereof.
[7] The therapeutic agent of [6], wherein the precursor is pri-miRNA or pre-miRNA of miR27b.
[8] The therapeutic agent of [1], wherein the tumor is a drug-resistant cancer.
[9] The therapeutic agent of [8], wherein the tumor is a drug-resistant breast cancer or drug-resistant lung cancer.
[10] The therapeutic agent of [1] for the suppression or prophylaxis of tumor metastasis.
[11] The therapeutic agent of [1] for the suppression or prophylaxis of cancer recurrence.
[12] The therapeutic agent of [11], wherein the cancer is breast cancer or lung cancer.
[13] A therapeutic agent for a tumor, comprising (A) a nucleic acid comprising miR27b or a nucleotide having a nucleotide sequence having an identity of 70% or more with the nucleotide sequence shown by SEQ ID NO: 1 and having a function equivalent to miR27b, and
(B) an antitumor agent
in combination.
[14] The therapeutic agent of [13], wherein the tumor is a drug-resistant cancer.
[15] The therapeutic agent of [13], wherein the tumor is a drug-resistant breast cancer or drug-resistant lung cancer.
[16] A method of determining a drug-resistant cancer, comprising measuring an expression level or concentration of miR27b in a tumor, and determining based on a negative correlation between the expression level or concentration and the drug resistance.
[17] A method of determining a cancer stem cell, comprising measuring an expression level of miR27b in a tumor.
[18] The method of [17], wherein the cancer stem cell is a breast cancer stem cell or lung cancer stem cell.
[19] A method of evaluating the prognosis of a cancer treatment, comprising measuring an expression level or concentration of miR27b in a tumor, and determining the presence or absence of a cancer stem cell.
[20] The method of [19], wherein the cancer stem cell is a breast cancer stem cell or lung cancer stem cell.
[21] An agent for determining a drug-resistant cancer, comprising a nucleic acid probe capable of specifically detecting miR27b.
[22] An agent for determining a cancer stem cell, comprising a nucleic acid probe capable of specifically detecting miR27b.
[23] The agent of [22], wherein the cancer stem cell is a breast cancer stem cell or lung cancer stem cell.
[24] A method of searching for a substance capable of suppressing the growth of a drug-resistant cancer, which comprises the following steps:
(1) contacting a test substance and a cell in which miR27b expression can be measured;
(2) measuring the level of miR27b expression in the cell contacted with the test substance, and comparing the expression level with the level of miR27b expression in a control cell free of contact with the test substance; and
(3) selecting a test substance that up-regulates the level of miR27b expression as the substance capable of inhibiting the growth of the drug-resistant cancer, based on the comparison results of the above-mentioned (2).
[25] A method of searching for a substance capable of inhibiting tumor metastasis or infiltration capability of a tumor cell, which comprises the following steps:
(1) contacting a test substance and a cell in which miR27b expression can be measured;
(2) measuring the level of miR27b expression in the cell contacted with the test substance, and comparing the expression level with the level of miR27b expression in a control cell free of contact with the test substance; and
(3) selecting a test substance that up-regulates the level of miR27b expression as the substance capable of inhibiting tumor metastasis or infiltration capability of a tumor cell, based on the comparison results of the above-mentioned (2).
[26] A method of treating a tumor in a mammal, comprising administering, to the mammal, an effective amount of a nucleic acid comprising miR27b or a nucleotide having a nucleotide sequence having an identity of 70% or more with the nucleotide sequence shown by SEQ ID NO: 1 and having a function equivalent to miR27b.
[27] The method of [26], wherein the tumor is a drug-resistant cancer.
[28] The method of [26], wherein the tumor is drug-resistant breast cancer or drug-resistant lung cancer.
[29] A method of suppressing or preventing tumor metastasis in a mammal, comprising administering, to the mammal, an effective amount of a nucleic acid comprising miR27b or a nucleotide having a nucleotide sequence having an identity of 70% or more with the nucleotide sequence shown by SEQ ID NO: 1 and having a function equivalent to miR27b.
[30] A method of suppressing or preventing cancer recurrence in a mammal, comprising administering, to the mammal, an effective amount of a nucleic acid comprising miR27b or a nucleotide having a nucleotide sequence having an identity of 70% or more with the nucleotide sequence shown by SEQ ID NO: 1 and having a function equivalent to miR27b.
[31] The method of [30], wherein the cancer is breast cancer or lung cancer.

[32] A method of treating a tumor in a mammal, comprising administering, to the mammal, an effective amount of
(A) a nucleic acid comprising miR27b or a nucleotide having a nucleotide sequence having an identity of 70% or more with the nucleotide sequence shown by SEQ ID NO: 1 and having a function equivalent to miR27b, and
(B) an antitumor agent.
[33] The method of [32], wherein the tumor is a drug-resistant cancer.
[34] The method of [32], wherein the tumor is drug-resistant breast cancer or drug-resistant lung cancer.
[35] A method of suppressing or preventing tumor metastasis in a mammal, comprising administering, to the mammal, an effective amount of
(A) a nucleic acid comprising miR27b or a nucleotide having a nucleotide sequence having an identity of 70% or more with the nucleotide sequence shown by SEQ ID NO: 1 and having a function equivalent to miR27b, and
(B) an antitumor agent.
[36] A method of suppressing or preventing cancer recurrence in a mammal, comprising administering, to the mammal, an effective amount of
(A) a nucleic acid comprising miR27b or a nucleotide having a nucleotide sequence having an identity of 70% or more with the nucleotide sequence shown by SEQ ID NO: 1 and having a function equivalent to miR27b, and
(B) an antitumor agent.
[37] The method of [36], wherein the cancer is breast cancer or lung cancer.

Effect of the Invention

The present invention can provide a therapeutic agent for tumor, particularly a therapeutic agent for drug-resistant cancer, an agent for suppression or prophylaxis of tumor metastasis, an agent for suppression or prophylaxis of cancer recurrence, and a medicament utilizing the aforementioned agent.
In addition, the present invention can also provide a method of determining a drug-resistant cancer, a method of determining a cancer stem cell, a method of evaluating the prognosis of cancer treatment, an agent for determining a drug-resistant cancer or a cancer stem cell, a method of screening for a substance having an action to suppress growth of a drug-resistant cancer, a method of screening for a substance having an action to inhibiting tumor metastasis and the like.

DESCRIPTION OF EMBODIMENTS

Figure 1:
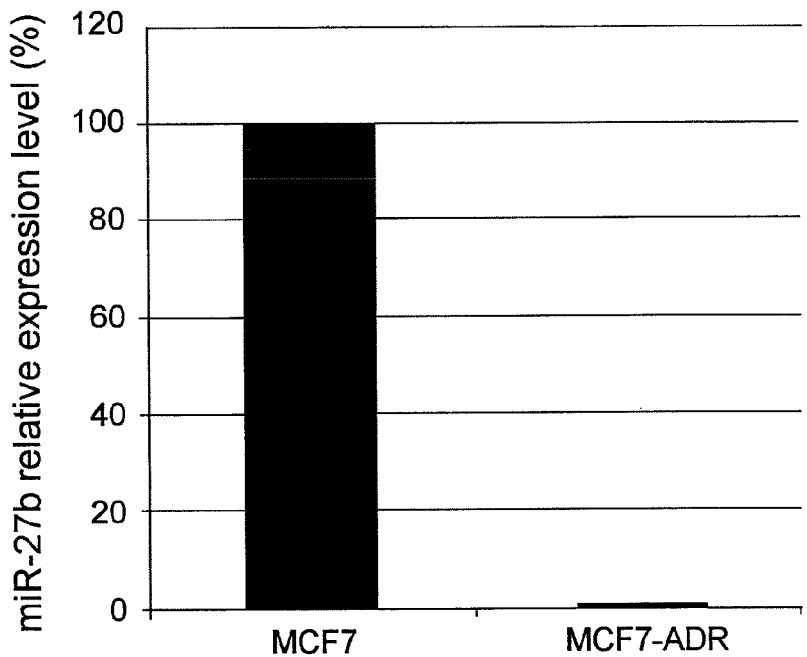
FIG. 1 shows the levels of miR27b expression in MCF7 cell and MCF7-ADR cell.

The present invention is explained in detail in the following.
1. Agent of the Present Invention
This time, the present inventors have found that miR27b (1) has a function to suppress growth of drug-resistant cancer cells (see Examples, described later), (2) has an activity to suppress RPN2 expression (see Examples, described later), and therefore, has a function to suppress metastasis of cancer cells, (3) is effective for a cancer stem cell differentiation therapy (see Examples, described later), and therefore, has a function to suppress or prevent cancer recurrence, and that miR27b can be utilized as an active ingredient of therapeutic agents for tumor.
That is, the present invention provides an agent containing a nucleic acid comprising miR27b or a nucleotide having a nucleotide sequence having an identity of 70% or more with the nucleotide sequence shown by SEQ ID NO: 1 and having a function equivalent to miR27b.
Accordingly, the agent of the present invention is useful as a therapeutic agent or a cell proliferation inhibitor for drug-resistant cancer, an agent for the suppression or prophylaxis of tumor metastasis, and an agent for the suppression or prophylaxis of cancer recurrence.
The nucleic acid of the present invention is RNA, a chimeric nucleic acid of RNA and DNA (hereinafter to be referred to as chimeric nucleic acid) or hybrid nucleic acid. Here, the chimeric nucleic acid means that RNA and DNA are contained in one nucleic acid of a single-stranded or double-stranded nucleic acid, and the hybrid nucleic acid means a nucleic acid wherein one of the double strands is RNA or chimeric nucleic acid and the other is DNA or chimeric nucleic acid.
The nucleic acid of the present invention is single-stranded or double-stranded. The embodiment of double-stranded includes double-stranded RNA, double-stranded chimeric nucleic acid, RNA/DNA hybrid, RNA/chimeric nucleic acid hybrid, chimeric nucleic acid/chimeric nucleic acid hybrid and chimeric nucleic acid/DNA hybrid. The nucleic acid of the present invention is preferably single-stranded RNA, single-stranded chimeric nucleic acid, double-stranded RNA, double-stranded chimeric nucleic acid, RNA/DNA hybrid, RNA/chimeric nucleic acid hybrid, chimeric nucleic acid/chimeric nucleic acid hybrid or chimeric nucleic acid/DNA hybrid, more preferably single-stranded RNA, single-stranded chimeric nucleic acid, double-stranded RNA, double-stranded chimeric nucleic acid, RNA/DNA hybrid, chimeric nucleic acid/chimeric nucleic acid hybrid or RNA/chimeric nucleic acid hybrid.
The length of the nucleic acid of the present invention has no upper limit as long as it has an activity to inhibit infiltration capability of tumor cell of a mammal (preferably human). In consideration of easiness of synthesis, antigenicity problem and the like, the length of the nucleic acid of the present invention is, for example, not more than about 200 bases, preferably not more than about 130 bases, more preferably not more than about 50 bases, most preferably not more than 30 bases. The lower limit is, for example, not less than 15 bases, preferably not less than 17 bases. The length of a nucleic acid having a double-stranded structure due to the hairpin loop structure of the nucleic acid is considered to be the length of a single strand.
miR27b is a molecule already known, and the representative one is called mature miRNA. Here, miR27b also includes miR27b isomer. Specifically, for example, it means a nucleotide consisting of the nucleotide sequence shown by SEQ ID NO: 1 (MIMAT0000419). The mature miR27b means a single-stranded or double-stranded RNA consisting of the nucleotide sequence shown by SEQ ID NO: 1.
The nucleic acid of the present invention shows, when incorporated into a tumor cell, an activity to suppress growth of a drug-resistant cancer cell, an activity to suppress infiltration capability of tumor cell, and an activity to suppress cancer recurrence. In the present invention, the "nucleotide having a function equivalent to miR27b" means one that forms a hybrid with a target mRNA of miR27b under biological conditions (for example, 0.1 M phosphate buffer (pH 7.0) 25° C.). Specifically, moreover, it means a nucleotide that forms a hybrid with a target mRNA of miR27b under biological conditions (for example, 0.1 M phosphate buffer (pH 7.0) 25° C.). Examples of the target mRNA of miR27b include RPN2, MDR1 and CD44. The "nucleotide having a function equivalent to miR27b" only needs to be a nucleotide that forms a hybrid with at least one target mRNA from among target mRNAs of miR27b and suppresses the function of the target mRNA.

The tumor cell is generally a cell of a mammal (e.g., rat, mouse, guinea pig, rabbit, sheep, horse, swine, bovine, monkey, human, preferably human). As the kind of the tumor, solid cancers such as breast cancer including mammary gland cancer and ductal breast cancer, lung cancer, pancreatic cancer, prostate cancer, osteosarcoma, esophagus cancer, liver cancer, gastric cancer, large intestine cancer, rectal cancer, colon cancer, urinary duct tumor, brain tumor, gall bladder cancer, bile duct cancer, biliary cancer, kidney cancer, bladder cancer, ovarian cancer, uterus cervix cancer, thyroid cancer, orchis tumor, Kaposi's sarcoma, maxilla cancer, tongue cancer, lip cancer, oral cancer, pharyngeal cancer, laryngeal cancer, myosarcoma, skin cancer and the like, myeloma, leukemia and the like can be recited as examples. The present invention is specifically effective for a drug-resistant cancer. Whether or not a nucleic acid has an activity to inhibit cell proliferation of a drug-resistant cancer can be confirmed by using a drug-resistant cancer cell line such as MCF7-ADR cell described in Example 1 and PC14-CDDP cell in Example 8. In addition, whether or not a nucleic acid has an activity to inhibit infiltration capability of tumor cell can be confirmed by, for example, the following assay.

To be specific, 143B cells which is a human osteosarcoma cell line having a metastatic ability is cultured overnight at $1 \times 10^6$ cells/6 cm dish, and nucleic acid is introduced to 30 nM by DharmaFECT transfection (manufactured by GE Healthcare Bioscience Inc.). Using the cells after 48 hr, cell infiltration assay is performed using a CytoSelect™ 96-Well Cell Invasion Assay kit (manufactured by Cell Biolab), and the infiltrated cells are counted after 20 hr.

The nucleotide sequence of the "nucleotide having a function equivalent to miR27b" used in the present invention has an identity of not less than 70%, preferably not less than 80%, more preferably not less than 90%, more preferably not less than 95%, with the nucleotide sequence shown by SEQ ID NO: 1.

The "identity" means the ratio (%) of the same nucleotide residues to the overlapping total nucleotide residues in an optimal alignment (preferably, the algorithm can consider introduction of a gap into one or both of the sequences for optimal alignment) when two nucleotide sequences are aligned using a mathematical algorithm known in the pertinent technical field.

In the present specification, the identity of nucleotide sequences can be calculated, for example, by aligning two nucleotide sequences using the homology calculation algorithm NCBI BLAST-2 (National Center for Biotechnology Information Basic Local Alignment Search Tool) under the following conditions (gap open=5 penalty; gap extension=2 penalty; x_dropoff=50; expectancy=10; filtering=ON).

Examples of the nucleotide sequence having an identity of not less than 70% with the nucleotide sequence shown by SEQ ID NO: 1 include the nucleotide sequence shown by SEQ ID NO: 1 wherein one or more nucleotides are deleted, substituted, inserted or added, such as (1) the nucleotide sequence shown by SEQ ID NO: 1 wherein 1-6 (preferably 1-3, more preferably 1 or 2) nucleotides are deleted, (2) the nucleotide sequence shown by SEQ ID NO: 1 wherein 1-6 (preferably 1-3, more preferably 1 or 2) nucleotides are added, (3) the nucleotide sequence shown by SEQ ID NO: 1 wherein 1-6 (preferably 1-3, more preferably 1 or 2) nucleotides are inserted, (4) the nucleotide sequence shown by SEQ ID NO: 1 wherein 1-6 (preferably 1-3, more preferably 1 or 2) nucleotides are substituted by other nucleotides, and (5) a nucleotide sequence wherein the above-mentioned mutations (1)-(4) are combined (in this case, the total of the mutated nucleotides is 1-6 (preferably 1-3, more preferably 1 or 2)).

The nucleotide sequence having an identity of not less than 70% with the nucleotide sequence shown by SEQ ID NO: 1 is preferably a partial sequence of not less than 15 contiguous bases (preferably not less than 17 bases, more preferably not less than 19 bases, most preferably 20 bases) contained in the nucleotide sequence shown by SEQ ID NO: 1, or a sequence containing same.

In the present specification, the nucleic acid comprising "miR27b" or "nucleotide having a function equivalent to miR27b" means that the nucleotide sequence of the nucleic acid contains the nucleotide sequence of "miR27b" or "nucleotide having a function equivalent to miR27b".

Since a natural nucleic acid is easily degraded by a nucleic acid degrading enzyme present in the cell, the nucleic acid of the present invention may be modified to be a modified product resistant to various degrading enzymes. The modified product of the present invention includes modified products within the range of a nucleotide having a nucleotide sequence having an identity of 70% or more with the nucleotide sequence shown by SEQ ID NO: 1 and having a function equivalent to miR27b, which are variously modified including modification of the sequence. Examples of the modification of the modified product include, but are not limited to, those wherein the sugar chain moiety is modified (e.g., 2'-O methylation), those wherein the base moiety is modified, and those wherein the phosphate moiety and hydroxyl moiety are modified (e.g., biotin, amino group, lower alkylamine group, acetyl group etc.).

In addition, the nucleic acid itself may be modified. Also, it may be a synthetic nucleic acid containing, for example, the same region as miR27b, and a complementary region complementary to 60%—less than 100% of the sequence. It may be a synthetic RNA molecule as described in WO 2006/627171.

The nucleic acid of the present invention may have an additional base at the 5'- or 3'-terminal. The length of the additional base is generally 5 bases or less. Although the additional base may be DNA or RNA, use of a DNA sometimes improves the stability of the nucleic acid. Examples of the sequences of such additional bases include, but are not limited to, the sequences ug-3', uu-3', tg-3', tt-3', ggg-3', guuu-3', gttt-3', ttttt-3', uuuuu-3' and the like.

A preferable embodiment of the nucleic acid of the present invention is a nucleic acid of mature miR27b, a precursor thereof and the like. Another preferable embodiment of the nucleic acid of the present invention is a nucleic acid containing a nucleotide having an activity similar to mature miRNA, such as miR27b mimic synthesized to mimic endogenous mature miR27b, and the like. A commercially available product can also be utilized. For example, Pre-miR™ miRNA precursor molecule (manufactured by Life Technologies: since Ambion became Life Technologies at the time point of September 2009 by merger and acquisition, the products of Ambion are described as manufactured by Life Technologies in the present specification).

The precursor of miR27b means nucleic acid capable of intracellularly producing mature miR27b as a result of intracellular processing, and cleavage of double-stranded nucleic acid. As the precursor, pri-miRNA, pre-miRNA and the like of miR27b can be mentioned. The pri-miRNA is a primary transcription product (single-stranded RNA) of miRNA gene, and generally has a length of about several hundred—several thousand bases. The pre-miRNA is a single-stranded RNA having a hairpin structure formed by intracellular processing of pri-miRNA, and generally has a length of 90-110 bases.

The pri-miRNA and pre-miRNA of miR27b are known molecules and are disclosed in, for example, miRBase database: http://microrna.sanger.ac.uk/ provided by Sanger Institute and the like. A preferable pre-miRNA of miR27b is, for example, a single-stranded RNA consisting of the nucleotide sequence shown by the following SEQ ID NO: 2 (MI0000440).

In addition, a single-stranded nucleic acid wherein, for example, the nucleotide sequence shown by SEQ ID NO: 1 (first sequence) and a complementary sequence thereof (second sequence) are linked via a hairpin loop region, which has a double-stranded structure of the first sequence and the second sequence due to the hairpin loop structure, is also one of the preferable embodiments of the nucleic acid of the present invention.

The nucleic acid of the present invention can be obtained by isolating from a mammalian cell (human cell etc.) or chemically synthesizing by a conventionally-known method, or by producing using a gene recombination technology. It is also possible to use a commercially available nucleic acid as appropriate. An miR27b mimic is available from, for example, Life Technologies and the like.

The agent of the present invention can contain any carrier, for example, a pharmaceutically acceptable carrier in addition to an effective amount of the nucleic acid of the present invention, and applied as a medicament in the form of a pharmaceutical composition.

Examples of the pharmaceutically acceptable carrier include, but are not limited to, excipients such as sucrose and starch; binders such as cellulose and methylcellulose; disintegrants such as starch and carboxymethylcellulose; lubricants such as magnesium stearate and Aerosil; flavoring agents such as citric acid and menthol; preservatives such as sodium benzoate and sodium hydrogen sulfite; stabilizers such as citric acid and sodium citrate; suspending agents such as methylcellulose and polyvinylpyrrolidone; dispersing agents such as surfactants; diluents such as water and physiological saline; base waxes; and the like.

To promote the introduction of the nucleic acid of the present invention into a cell, the agent of the present invention can further comprise a reagent for nucleic acid introduction. As the reagent for nucleic acid introduction, atelocollagen; liposome; nanoparticle; cationic lipid such as lipofectin, lipofectamine, DOGS (transfectam), DOPE, DOTAP, DDAB, DHDEAB, HDEAB, polybrene, or poly(ethyleneimine) (PEI) and the like; and the like can be used.

When the agent of the present invention is contained in atelocollagen, the nucleic acid of the present invention can be efficiently delivered to a target tumor cell and can be efficiently incorporated into the cell.

While the agent of the present invention can be orally or parenterally administered to a mammal, it is desirably administered parenterally.

Preparations suitable for parenteral administration (for example, subcutaneous injection, intramuscular injection, topical injection, intraperitoneal administration and the like) include aqueous and non-aqueous isotonic sterile injectable liquids, which may contain an antioxidant, a buffer solution, a bacteriostatic agent, an isotonizing agent and the like. Aqueous and non-aqueous sterile suspensions can also be mentioned, which may contain a suspending agent, a solubilizer, a thickening agent, a stabilizer, an antiseptic and the like. These preparations can be encapsulated in containers such as ampoules and vials for unit dosage or a plurality of dosages. It is also possible to freeze-dry the active ingredient and a pharmaceutically acceptable carrier, and store the preparation in a state that may be dissolved or suspended in an appropriate sterile vehicle just before use.

As other preparations preferable for parenteral administration, spray and the like can be mentioned.

The content of the nucleic acid of the present invention in a pharmaceutical composition is, for example, about 0.1% to 100% by weight of the entire pharmaceutical composition.

While the dose of the agent of the present invention varies depending on the administration object, administration method, the kind and size of tumor, condition of the subject of administration (sex, age, body weight and the like), generally, it is desirably not less than 1 pmol/kg and not more than 10 nmol/kg for topical administration to an adult by injection and not less than 2 nmol/kg and not more than 50 nmol/kg for systemic administration to an adult, in the amount of the nucleic acid of the present invention. Such dose is desirably administered in 1-10 portions, more preferably 5-10 portions.

The agent of the present invention is safely administered to a mammal (e.g., rat, mouse, guinea pig, rabbit, sheep, horse, swine, bovine, monkey, human) such that the nucleic acid of the present invention, which is the active ingredient, is delivered to a tumor tissue (tumor cell).

Since the nucleic acid of the present invention has an activity to suppress cell proliferation in a drug-resistant cancer and an activity to suppress MDR1 expression, a drug-resistant cancer disease can be treated by administering the agent of the present invention to patients with a drug-resistant cancer and the like.

Since the nucleic acid of the present invention has an RPN2 expression suppressive activity, tumor metastasis can be suppressed and diseases caused by tumor metastasis can be treated or prevented by administering the agent of the present invention to tumor patients, patients after a treatment of tumor who have a risk of tumor metastasis and the like.

Furthermore, the nucleic acid of the present invention has an activity to change, as described in the Examples, a cancer stem cell to a non-cancer stem cell. Cancer stem cells are resistant to general antitumor agents and are said to be deeply involved in the recurrence and metastasis of tumor (Takao Setoguchi et al., Protein Nucleic acid and Enzyme, Vol. 50 No. 15 1999 (2005), Keisuke Ieda et al., *Gan Bunnshi Hyouteki Chiryo* (Cancer Molecule Target Treatment), Vol. 5 No. 3 187 (2007)), cancer stem cell count in a tumor can be decreased and cancer recurrence and metastasis can be suppressed or prevented by administering the agent of the present invention to tumor patients.

Therefore, the agent of the present invention is extremely useful as a therapeutic agent for tumor.

Here, the "drug-resistant cancer" means a cancer resistant to anti-cancer agents.

The "suppression of metastasis" means suppression of a tumor cell reaching a different region from the primary lesion and secondarily developing the tumor at the region.

The "cancer stem cell" means a cell having self-replication capacity and cancer forming ability in combination, which is resistant to anti-cancer agents and radiation therapy and is a causative cell of cancer recurrence.

Examples of the tumor to which the agent of the present invention can be applied include solid cancers such as breast cancer, lung cancer, pancreatic cancer, prostate cancer, osteosarcoma, esophagus cancer, liver cancer, gastric cancer, large intestine cancer, rectal cancer, colon cancer, urinary duct tumor, brain tumor, gall bladder cancer, bile duct cancer, biliary cancer, kidney cancer, bladder cancer, ovarian cancer, uterus cervix cancer, thyroid cancer, orchis tumor, Kaposi's sarcoma, maxilla cancer, tongue cancer, lip cancer, mouth cavity cancer, pharyngeal cancer, laryngeal cancer, myosarcoma, skin cancer, retinoblastoma and the like, myeloma, leukemia, malignant lymphoma, myeloma, malignant melanoma, Hemangioma, polycythemia vera, neuroblastoma and the like. Specifically, a drug-resistant cancer, metastatic cancer, and a cancer having a risk of cancer recurrence are preferable.

Examples of the drug-resistant cancer include drug resistant cancers from among the aforementioned tumors. Preferred are drug resistant breast cancer, drug resistant lung cancer, and more preferred is drug resistant mammary gland cancer (ductal breast cancer).

Examples of the metastatic cancer include metastatic cancers of breast cancer, lung cancer, pancreatic cancer, prostate cancer, kidney cancer, multiple myeloma, thyroid cancer, adenocarcinoma, blood cell malignant tumor including leukemia and lymphoma; head and neck cancer; gastrointestinal tract cancer including gastric cancer, colon cancer, colorectal cancer, liver cancer; female genital tract malignant tumor including ovarian cancer, endometrium cancer, and uterus cervix cancer; bladder cancer; brain tumor including neuroblastoma; sarcoma, osteosarcoma; and skin cancer including malignant melanoma and squamous cell carcinoma, and the like, and preferred are metastatic cancers of breast cancer and lung cancer.

Examples of the diseases caused by tumor metastasis include metastatic cancer, respiratory insufficiency caused by tumor increase and carcinomatous pleurisy, and the like.

The cancer with the risk of cancer recurrence is a cancer having a risk of recurrence of cancer after cancer treatment or surgery. The cancer having a risk of recurrence is exemplified by the aforementioned cancers with a risk of cancer recurrence, and preferred are breast cancer and lung cancer with the risk of cancer recurrence.

The agent of the present invention is desirably administered to patients showing a decreased miR27b expression level in a tumor tissue.

2. Combined Use of Nucleic Acid of the Present Invention and Antitumor Agent

Using the nucleic acid of the present invention and an antitumor agent in combination, growth of the tumor itself can be suppressed, as well as the effects of suppression of the growth of a drug-resistant cancer, suppression of tumor metastasis, and decrease of cancer stem cell count can be obtained. Therefore, the tumor can be treated definitively. Accordingly, the present invention provides a tumor therapeutic agent containing the aforementioned nucleic acid of the present invention and an antitumor agent in combination.

While the antitumor agent usable for the concomitant drug for the present invention is not particularly limited, one having an activity to suppress growth of the tumor itself is preferable. As such antitumor agent, microtubule acting drugs such as taxanes and the like, as well as metabolic antagonist, DNA alkylating agent, DNA binding agent (platinum preparation), anti-cancer antibiotic and the like can be mentioned. Specifically, amrubicin hydrochloride, irinotecan hydrochloride, ifosfamide, etoposide Lastet, Gefitinib, cyclophosphamide, cisplatin, trastuzumab, fluorouracil, mitomycin C, imatinib mesylate, methotrexate, Rituxan, adriamycin and the like can be mentioned.

For combined use of the nucleic acid of the present invention and an antitumor agent, the administration time of the nucleic acid of the present invention and an antitumor agent is not restricted, and the nucleic acid of the present invention or the antitumor agent can be administered to an administration subject simultaneously, or may be administered at different times.

As the subject of administration, drug-resistant cancer patients, metastatic cancer patients, cancer recurrence patients, patients with a risk of cancer recurrence can be preferably mentioned.

The agent of the present invention is desirably administered to patients showing a decreased expression level of miR27b in tumor tissues.

The dose of the nucleic acid of the present invention is not particularly limited as long as the applicable disease can be prevented or treated, and administration within the dose range described in the above-mentioned (1. the agent of the present invention) is possible.

The dose of an antitumor agent can be determined according to the dose clinically employed for the administration of the antitumor agent as a single agent.

The administration mode of the nucleic acid of the present invention and the antitumor agent is not particularly restricted, and it is sufficient that the nucleic acid of the present invention and the antitumor agent are combined in administration. Examples of such administration mode include the following:
(1) administration of a single preparation obtained by simultaneously processing the nucleic acid of the present invention and the antitumor agent, (2) simultaneous administration of two kinds of preparations of the nucleic acid of the present invention and the antitumor agent, which have been separately produced, by the same administration route, (3) administration of two kinds of preparations of the nucleic acid of the present invention and the antitumor agent, which have been separately produced, by the same administration route in a staggered manner, (4) simultaneous administration of two kinds of preparations of the nucleic acid of the present invention and the antitumor agent, which have been separately produced, by different administration routes, (5) administration of two kinds of preparations of the nucleic acid of the present invention and the antitumor agent, which have been separately produced, by different administration routes in a staggered manner (for example, administration in the order of the nucleic acid of the present invention and the antitumor agent, or in the reverse order) and the like.

An agent containing the nucleic acid of the present invention and an antitumor agent in combination can be formulated by a conventional method, according to the description in the above-mentioned (1. the agent of the present invention). When the nucleic acid of the present invention and an antitumor agent are separately formulated, the dosage form of the antitumor agent can be determined according to the dosage form clinically employed for the administration of the antitumor agent as a single agent.

For administration of a combination of the aforementioned nucleic acid of the present invention and an antitumor agent, which are separately formulated, a preparation containing the nucleic acid of the present invention may be administered after administration of a preparation containing an antitumor agent or a preparation containing an antitumor agent may be administered after administration of a preparation containing the nucleic acid of the present invention, though they may be administered simultaneously. When administered at a time interval, the interval differs depending on the effective ingredient to be administered, drug form and administration method, and for example, when a preparation containing an antitumor agent is administered first, a method in which a preparation containing the nucleic acid of the present invention is administered within time range of from 1 min to 3 days, preferably from 10 min to 1 day, more preferably from 15 min to 1 hr after administration of the preparation containing an antitumor agent is exemplified. When a preparation containing the nucleic acid of the present invention is administered first, a method in which a preparation containing an antitumor agent is administered within time range of from 1 min to 1 day, preferably from 10 min to 6 hrs, more preferably from 15 min to 1 hr after administration of a preparation containing the nucleic acid of the present invention is exemplified.

The concomitant drug for the present invention may contain two or more kinds of antitumor agents.

The concomitant drug for the present invention can be applied to the tumors described in detail as the "tumor to which the agent of the present invention can be applied" in the above-mentioned (1. the agent of the present invention). The concomitant drug for the present invention is preferably applied specifically to a drug-resistant cancer, a metastatic cancer or a cancer with a risk of recurrence.

3. Method for Determining Drug-Resistant Cancer

The present invention provides a method of determining a drug-resistant cancer, comprising measuring the level of miR27b expression in a tumor, and determining whether it is a drug-resistant cancer based on a negative correlation between the expression level and drug resistance.

In the determination method of the present invention, the level of miR27b expression of a tumor tissue or tumor cell from the tumor isolated from the measurement target patient is measured. The kind of tumor to which the determination method of the present invention can be applied includes the tumors described in detail as the "tumor to which the agent of the present invention can be applied" in the above-mentioned (1. the agent of the present invention). The determination method of the present invention can be preferably applied to lung cancer and breast cancer.

The determination method of the present invention measures the expression level of miR27b including mature form, pri-miRNA and pre-miRNA. Preferably measured is the total of the expression levels of all these forms or expression level of the mature form, more preferably measured is the expression level of the mature form.

For example, the level of miR27b expression can be measured by a method known per se and using a nucleic acid probe capable of specifically detecting the miRNA. Examples of the measurement method include RT-PCR, Northern blotting, in situ hybridization, nucleic acid array and the like. Alternatively, it can also be measured by a commercially available kit (e.g., TaqMan (registered trade mark) MicroRNA Cells-to-CT™ Kit).

As a nucleic acid probe capable of specifically detecting miR27b, a polynucleotide containing not less than 15 bases, preferably not less than 18 bases, more preferably not less than about 20 bases, most preferably the full-length continuous nucleotide sequence of the nucleotide sequence shown by SEQ ID NO: 1, or a complementary sequence thereof, can be mentioned.

The nucleic acid probe may contain an additional sequence (nucleotide sequence not complementary to the detection target polynucleotide) as long as the specific detection is not impaired.

In addition, the nucleic acid probe may be labeled with a suitable label, for example, radioisotope (e.g., $^{125}$I, $^{131}$I, $^{3}$H, $^{14}$C etc.), enzyme (e.g., β-galactosidase, β-glucosidase, alkaline phosphatase, peroxidase, malate dehydrogenase etc.), fluorescent substance (e.g., fluorescamine, fluorescein isothiocyanate etc.), luminescent substance (e.g., luminol, luminol derivative, luciferin, lucigenin etc.) and the like. Alternatively, a quencher (quenching substance) that absorbs fluorescence energy emitted by a fluorescent substance (e.g., FAM, VIC etc.) may be further bonded in the vicinity of the fluorescent substance. In such embodiment, fluorescence is detected during a detection reaction due to the separation of fluorescent substance and quencher.

The nucleic acid probe may be any of DNA, RNA and chimeric nucleic acid, and may be single-stranded or double-stranded. The nucleic acid probe or primer can be synthesized based on, for example, the information of the nucleotide sequence shown by SEQ ID NO: 1 or 2 and using a DNA/RNA automatic synthesizer, according to a conventional method.

Then, based on the measured level of miR27b expression, whether or not the tumor is a drug-resistant cancer is determined. As shown in the below-mentioned Examples, a drug-resistant cancer cell shows low level of miR27b expression, as compared to drug-non-resistant cancer cells. The above-mentioned determination is based on a negative correlation between the level of miR27b expression and the drug resistance.

For example, tumor is isolated (or tumor cell is obtained) from a patient with cancer other than drug-resistant cancer (negative control) and a drug-resistant cancer patient (positive control), and the level of miR27b expression of a target patient is compared with that of the positive control and the negative control. Alternatively, a correlation chart of the level of miR27b expression in tumor and drug-resistant cancer is prepared in advance, and the level of miR27b expression in the tumor (or tumor cell) isolated from a target patient may be compared with the correlation chart. The expression level is compared preferably based on the presence or absence of a significant difference.

When the level of miR27b expression of the measurement target is relatively low based on the comparison results of the miR27b expression level, the possibility of the tumor being a drug-resistant cancer can be determined to be relatively high. Conversely, when the level of miR27b expression of the measurement target is relatively high, the possibility of the tumor being a drug-resistant cancer can be determined to be relatively low.

Since the treatment target of the therapeutic agent of the present invention is desirably a drug-resistant cancer patient showing a low expression level of miR27b in a tumor tissue (or tumor cell), the method of the present invention is useful for selection of the patients.

The present invention also provides an agent for evaluating a drug-resistant cancer, containing a nucleic acid probe capable of specifically detecting the aforementioned miR27b (hereinafter to be referred to as "the agent (II) of the present invention"). The agent (II) of the present invention can be a kit for evaluating the drug resistance of a tumor. Using the agent (II) of the present invention, whether or not the tumor is drug resistant can be evaluated easily by the aforementioned evaluation method.

A nucleic acid probe is generally contained in the agent (II) of the present invention in the form of an aqueous solution wherein the nucleic acid probe is dissolved in water or a suitable buffer (e.g., TE buffer, PBS and the like) to a suitable concentration, or a nucleic acid array wherein the nucleic acid probe is immobilized on a solid phase carrier.

The agent (II) of the present invention may further contain, as a constitution, other components necessary for practicing the measurement method of miR27b. For example, when Northern blotting or nucleic acid array is used for the measurement, the agent (II) of the present invention can further contain a blotting buffer, a labeling reagent, a blotting membrane and the like. When in situ hybridization is used for the measurement, the agent (II) of the present invention can further contain a labeling reagent, a color development substrate and the like.

4. Method for Determining Cancer Stem Cell

The present invention provides a method of determining a cancer stem cell, including measuring the level of miR27b expression in a tumor cell, and determining whether it is a cancer stem cell based on a negative correlation between the expression level and the cancer stem cell.

In the determination method of the present invention, the expression level or concentration of miR27b in a tumor tissue or tumor cell from the tumor isolated from the measurement target patient is measured. The kind of tumor to which the determination method of the present invention can be applied includes the tumors described in detail as the "tumor to which the agent of the present invention can be applied" in the above-mentioned (1. the agent of the present invention). The determination method of the present invention can be preferably applied to a cancer wherein a cancer stem cell is characterized by CD44 expression (e.g., breast cancer, prostate cancer, pancreatic cancer, head and neck squamous cell cancer, lung cancer and the like), more preferably breast cancer and lung cancer.

The determination method of the present invention measures the expression level or concentration of miR27b including mature form, pri-miRNA and pre-miRNA. Preferably measured is the total of the expression levels of all these forms or expression level of the mature form, more preferably measured is the expression level of the mature form.

For example, the expression level and concentration of miR27b can be measured by a method known per se and using a nucleic acid probe capable of specifically detecting the miRNA. Examples of the measurement method include RT-PCR, Northern blotting, in situ hybridization, nucleic acid array and the like. Alternatively, it can also be measured by a commercially available kit (e.g., TaqMan (registered trademark) MicroRNA Cells-to-CT™ Kit).

As a nucleic acid probe capable of specifically detecting miR27b, a polynucleotide containing not less than 15 bases, preferably not less than 18 bases, more preferably not less than about 20 bases, most preferably the full-length continuous nucleotide sequence of the nucleotide sequence shown by SEQ ID NO: 1, or a complementary sequence thereof, can be mentioned.

The nucleic acid probe may contain an additional sequence (nucleotide sequence not complementary to the detection target polynucleotide) as long as the specific detection is not impaired.

In addition, the nucleic acid probe may be labeled with a suitable label, for example, radioisotope (e.g., $^{125}$I, $^{131}$I, $^3$H, $^{14}$C etc.), enzyme (e.g., β-galactosidase, β-glucosidase, alkaline phosphatase, peroxidase, malate dehydrogenase etc.), fluorescent substance (e.g., fluorescamine, fluorescein isothiocyanate etc.), luminescent substance (e.g., luminol, luminol derivative, luciferin, lucigenin etc.) and the like. Alternatively, a quencher (quenching substance) that absorbs fluorescence energy emitted by a fluorescent substance (e.g., FAM, VIC etc.) may be further bonded in the vicinity of the fluorescent substance. In such embodiment, fluorescence is detected during a detection reaction due to the separation of fluorescent substance and quencher.

The nucleic acid probe may be any of DNA, RNA and chimeric nucleic acid, and may be single-stranded or double-stranded. The nucleic acid probe or primer can be synthesized based on, for example, the information of the nucleotide sequence shown by SEQ ID NO: 1 or 2 and using a DNA/RNA automatic synthesizer, according to a conventional method.

Then, based on the measured expression level or concentration of miR27b, whether or not the cell is a cancer stem cell is determined. As shown in the below-mentioned Examples, a cancer stem cell shows a low level of miR27b expression. The above-mentioned determination is based on such negative correlation between the expression level or concentration of miR27b and cancer stem cell of tumor. When the expression level or concentration of miR27b of the measurement target is relatively low based on the comparison results of the expression level or concentration of miR27b, the cell is determined to be a cancer stem cell.

Since the presence or absence of cancer stem cell of the tumor of patient after a treatment with an antitumor agent is considered to show a positive correlation with the risk of cancer recurrence and the risk of development of tumor metastasis, the prognosis of the patient can be predicted by measuring the presence or absence of cancer stem cell.

The present invention also provides an agent for determining a cancer stem cell, containing a nucleic acid probe capable of specifically detecting the aforementioned miR27b (hereinafter to be referred to as "the agent (III) of the present invention"). The agent (III) of the present invention can be a kit for evaluating the risk of cancer recurrence or life prognosis of cancer patient. Using the agent (III) of the present invention, the prognosis of cancer patient can be evaluated easily by the aforementioned determination method.

A nucleic acid probe is generally contained in the agent (III) of the present invention in the form of an aqueous solution wherein the nucleic acid probe is dissolved in water or a suitable buffer (e.g., TE buffer, PBS and the like) to a suitable concentration, or a nucleic acid array wherein the nucleic acid probe is immobilized on a solid phase carrier.

The agent (III) of the present invention may further contain, as a constitution, other components necessary for practicing the measurement method of miR27b. For example, when Northern blotting or nucleic acid array is used for the measurement, the agent (III) of the present invention can further contain a blotting buffer, a labeling reagent, a blotting membrane and the like. When in situ hybridization is used for the measurement, the agent (III) of the present invention can further contain a labeling reagent, a color development substrate and the like.

5. Method of Searching for a Substance Capable of Suppressing the Growth of Drug-Resistant Cancer, a Substance Capable of Inhibiting Tumor Metastasis or Infiltration Capability of a Tumor Cell and the Like The present invention also provides a method of searching for a substance capable of suppressing the growth of a drug-resistant cancer, a method of searching for a substance capable of inhibiting tumor metastasis or infiltration capability of a tumor cell, and a method of searching for a substance capable of turning a cancer stem cell to a non-cancer stem cell, comprising evaluating whether or not a test substance potentiates miR27b expression, and substances obtained by the methods. In the search methods of the present invention, a substance that up-regulates miR27b expression is selected as a substance capable of suppressing the growth of a drug-resistant cancer, a substance capable of inhibiting tumor metastasis or infiltration capability of a tumor cell, or a cancer stem cell function inhibitor.

The test substance subjected to the screening method of the present invention may be any commonly known compound or a novel compound; examples include nucleic acids, sugars, lipids, proteins, peptides, organic low molecular compounds, compound libraries prepared using combinatorial chemistry technology, random peptide libraries, or naturally occurring ingredients derived from microorganisms, animals, plants, marine organisms and the like, and the like.

The search method of the present invention comprises the following steps:
(1) contacting a test substance and a cell in which miR27b expression can be measured;
(2) measuring the level of miR27b expression in the cell contacted with the test substance, and comparing the expression level with the level of miR27b expression in a control cell free of contact with the test substance; and
(3) selecting a test substance that up-regulates the level of miR27b expression as the substance capable of inhibiting tumor metastasis or infiltration capability of a tumor cell, based on the comparison results of the above-mentioned (2).

The search method of the present invention measures the expression level of miR27b including mature form, pri-miRNA and pre-miRNA. Preferably measured is the total of the expression levels of all these forms or expression level of the mature form, more preferably measured is the expression level of the mature form.

The "cell in which expression can be measured" refers to a cell in which the expression level of miRNA of a measurement target can be evaluated. As the cell, a cell capable of naturally expressing miRNA of a measurement target can be mentioned.

A cell capable of naturally expressing the measurement target, namely, miR27b, is not particularly limited as long as it potentially expresses miR27b. As the cell, a primary cultured cell of a mammal (for example, human, mouse etc.), a cell induced from the primary cultured cell and the like can be used. Examples of the cell capable of naturally expressing miR27b include cells of the tumors described in detail as the "tumor to which the agent of the present invention can be applied" in the above-mentioned (1. the agent of the present invention) (breast cancer cell and lung cancer cell). Preferred are breast cancer cell and lung cancer cell, and more preferred are drug resistant breast cancer cell and drug resistant lung cancer cell.

A test substance and a cell in which miR27b expression can be measured are brought into contact in a culture medium. While the culture medium is appropriately selected according to the cell permitting natural expression of miR27b, it is, for example, minimum essential medium (MEM), Dulbecco's modified Eagle medium (DMEM) and the like, containing about 5-20% of fetal bovine serum. While the culture conditions are also determined as appropriate, for example, the pH of the medium is about 6 to about 8, cultivation temperature is generally about 30° C. to about 40° C., and cultivation time is about 12 to about 72 hours.

The level of miR27b expression can be measured according to the method described in (3. Method of determining drug-resistant cancer).

This comparison of the expression level can be preferably performed on the basis of the presence or absence of a significant difference. Although the level of miR27b expression in the control cells not contacted with the test substance may be measured before or simultaneously with the measurement of the level of miR27b expression in the cells contacted with the test substance, it is preferable, from the viewpoint of experimental accuracy and reproducibility, that the level of miR27b expression in the control cells be a simultaneously measured.

A substance that up-regulates the level of miR27b expression, which is obtained as a result of comparison, is selected as a substance capable of suppressing growth of a drug-resistant cancer cell, a substance capable of inhibiting tumor metastasis or infiltration capability of a tumor cell, or a therapeutic agent for cancer stem cell.

The compound obtained by the search method of the present invention is useful as a candidate substance for the development of a new therapeutic agent for tumor.

In the Sequence Listing of the present invention, the nucleotide sequences are conveniently described using RNA sequences. This does not mean that the nucleic acid specified by SEQ ID NO shows RNA alone, but also shows nucleotide sequences of DNA and chimeric nucleic acids as appropriate by reading U (uracil) as T (thymine).

EXAMPLES

The present invention is explained in the following by referring to Examples, which are not to be construed as limitative.

Reference Example 1

Expression of miR27b in Drug Resistant MCF7 Cell (MCF7-ADR Cell)

MCF7 cell and MCF7-ADR cell were cultivated in DMEM medium supplemented with 10% fetal bovine serum (FBS), microRNAs were extracted from the both cell lines by using a mirVana RNA Isolation kit (manufactured by Life Technologies), according to the protocol attached to the kit. Using the obtained microRNA as a template, TaqMan MicroRNA Reverse Transcription kit (manufactured by Life Technologies), and miR27b TaqMan MicroRNA Assay or U6 TaqMan MicroRNA Assay (manufactured by Life Technologies), reverse transcription reaction was performed. That is, microRNA (5 μL), 100 mM dNTPs (with dTTP) (0.15 μL), MultiScribe Reverse Transcriptase (50 U/μL) (1 μL), 10× Reverse Transcription Buffer (1.5 μL), RNase Inhibitor (20 U/μL) (0.19 μL), Nuclease-free water (4.16 μL), and TaqMan MicroRNA Assay (5×) (3 μL) were mixed, and the mixture was incubated at 16° C. for 30 min, at 42° C. for 30 min, and at 85° C. for 5 min. A 15-fold diluted solution (1.33 μL) of the reaction mixture, TaqMan MicroRNA Assay (20×) (1 μL), TaqMan 2× Universal PCR Master Mix, No AmpErase UNGa (manufactured by Life Technologies) (10 μL), and Nuclease-free water (7.67 μL) were mixed and, after incubation at 95° C. for 10 min, a PCR reaction including 40 repeats of an incubation cycle at 95° C. for 15 sec, and at 60° C. for 1 min was performed using a 7300 Real Time PCR System (manufactured by Life Technologies) and the expression levels of miR27b, U6 in MCF7, MCF7-ADR cells were quantified. As a result, as shown in FIG. 1, the level of miR27b expression in MCF7-ADR cell was found to have decreased as compared to MCF7 cell.

Example 1

RPN2 Expression-Suppressive Activity of miR27b (1) Construction of FLuc-hRPN2-3' UTR A reaction mixture (20 μL) containing human breast cancer cDNA library solution (2 μL), a primer consisting of a base sequence shown by SEQ ID NO: 3 (100 pmol), a primer consisting of a base sequence shown by SEQ ID NO: 4 (100 pmol), Taq polymerase (manufactured by Life Technologies) (0.1 μL), Taq polymerase-attached buffer (2 μL) and Taq polymerase-attached dNTP mixture (2 μL) was prepared. PCR was performed under the conditions of a treatment at 95° C. for 9 min, then 25 repeats of an incubation cycle at 95° C. for 30 sec, at 62° C. for 30 sec, and at 72° C. for 1 min, and lastly an incubation at 72° C. for 5 min. After PCR, an about 281 bp PCR product was recovered by agarose electrophoresis. The recovered PCR product was subcloned to XbaI site of pGL-3 vector (manufactured by Promega), and *E. coli* DH5α strain competent cell (manufactured by TOYOBO) was transformed with the plasmid. The transformed cells were cultivated in 50 μg/mL kanamycin-containing LB medium (100 mL), and the obtained cultivated bacteria were used for separation and purification using a QIAGEN Plasmid Maxi kit (manufactured by QIAGEN) to give plasmid FLuc-hRPN2-3' UTR wherein 3' UTR region of human-derived RPN2 gene is linked to the 3' side of Firefly luciferase gene. Using the obtained plasmid as a template, BigDye® Terminator v3.1 Cycle Sequencing kit (manufactured by Life Technologies) and ABI PRISM (registered trade mark) 3100 Genetic Analyzer sequence reader (manufactured by Life Technologies), the base sequence of 3' UTR region of human-derived RPN2 gene consisting of the base sequence shown by SEQ ID NO: 5 was determined.

(2) Luciferase Assay

Figure 2:
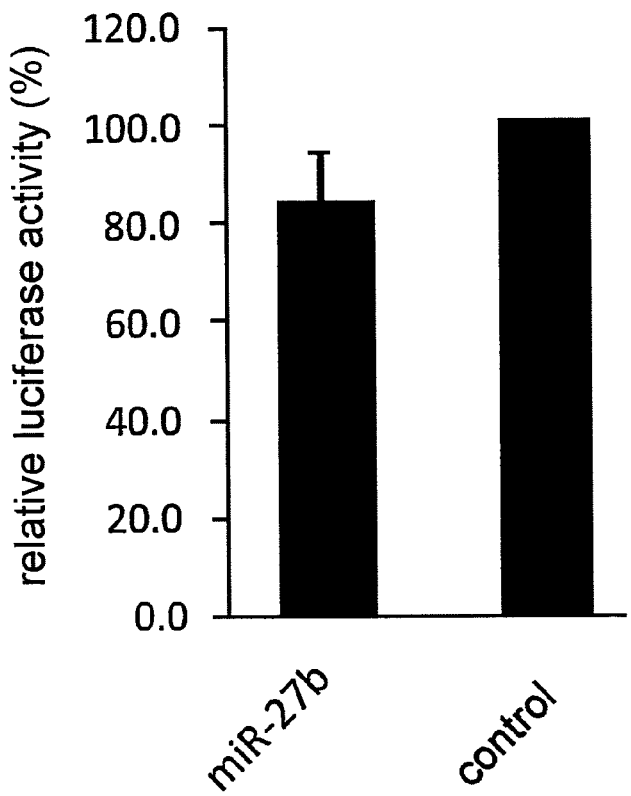
FIG. 2 shows suppression of RPN2 expression by miR27b.

Then, RPN2 expression suppressive activity of miR27b was evaluated using FLuc-hRPN2-3' UTR obtained by the method described in the above-mentioned (1). MCF7-ADR cells (100 μl) prepared to 50000 cells/ml were seeded on a 96-well plate and incubated overnight at 37° C. The next day, FLuc-hRPN2-3' UTR (300 ng), *Renilla* luciferase expression vector (50 ng), and 2 μM Pre-miR™ miRNA27b Precursor Molecule (manufactured by Life Technologies) or Pre-miR™ miRNA Precursor Molecules-Negative Control (NC1) (manufactured by Life Technologies) (1 μl) were transfected to the aforementioned cells by using a Lipofectamine 2000 reagent (manufactured by Invitrogen). The cells were cultured in the presence of 5% $CO_2$ at 37° C. for 1 day, and the expression level of firefly and *Renilla* luciferase was measured by using Dual-Glo Luciferase Assay System (manufactured by Promega) and Envision 2101 Multilabel Reader (manufactured by PerkinElmer). As a result, the luciferase activity of the cells introduced with Pre-miR™ miRNA27b Precursor Molecule (manufactured by Life Technologies) was found to have decreased as compared to the cells introduced with a control, Pre-miR™ miRNA Precursor Molecules-Negative Control (NC1) (manufactured by Life Technologies) (FIG. 2). That is, miR27b was shown to suppress RPN2 expression.

Example 2

MDR1 Expression Suppressive Activity of miR27b (1) Construction of FLuc-hMDR1-3' UTR A reaction mixture (20 μL) containing MCF7-ADR-derived cDNA library solution (2 μL), a primer consisting of a base sequence shown by SEQ ID NO: 6 (100 pmol), a primer consisting of a base sequence shown by SEQ ID NO: 7 (100 pmol), Taq polymerase (manufactured by Life Technologies) (0.1 μL), Taq polymerase-attached buffer (2 μL) and Taq polymerase-attached dNTP mixture (2 μL) was prepared. PCR was performed under the conditions of a treatment at 95° C. for 9 min, then 25 repeats of an incubation cycle at 95° C. for 30 sec, at 62° C. for 30 sec, and at 72° C. for 1 min, and lastly an incubation at 72° C. for 5 min. After PCR, an about 575 bp PCR product was recovered by agarose electrophoresis. The recovered PCR product was subcloned to XbaI site of pGL3 vector (manufactured by Promega), and *E. coli* DH5α strain competent cell (manufactured by TOYOBO) was transformed with the plasmid. The transformed cells were cultivated in 50 μg/ml kanamycin-containing LB medium (100 mL), and the obtained cultivated bacteria were used for separation and purification using a QIAGEN Plasmid Maxi kit (manufactured by QIAGEN) to give plasmid FLuc-hMDR1-3' UTR wherein 3' UTR region of human-derived RPN2 gene is linked to the 3' side of Firefly luciferase gene. Using the obtained plasmid as a template, BigDye (registered trade mark) TeLminator v3.1 Cycle Sequencing kit (manufactured by Life Technologies) and ABI PRISM (registered trade mark) 3100 Genetic Analyzer sequence reader (manufactured by Life Technologies), the base sequence of 3' UTR region of human-derived MDR1 gene consisting of the base sequence shown by SEQ ID NO: 8 was determined.

(2) Luciferase Assay

Figure 3:
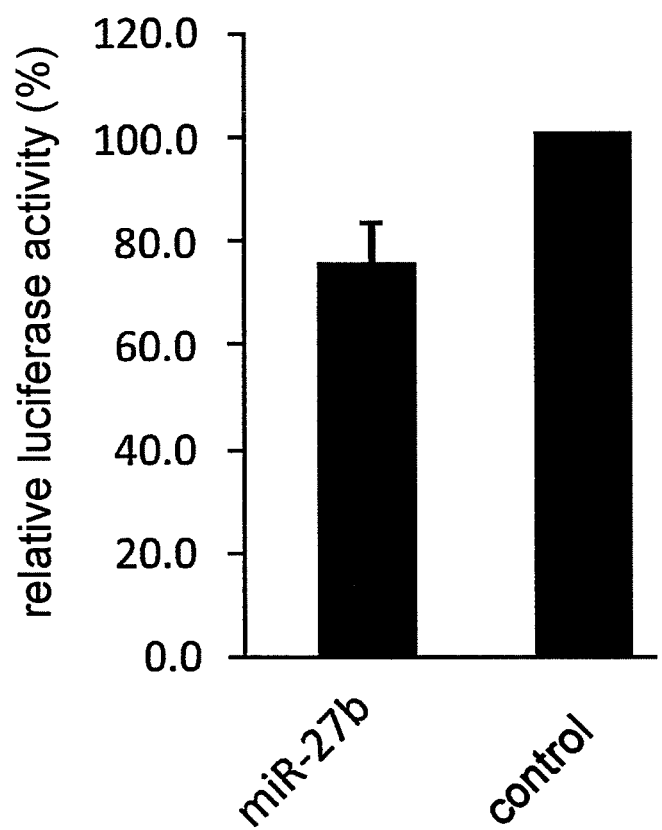
FIG. 3 shows suppression of MDR1 expression by miR27b.

Then, MDR1 expression suppressive activity of miR27b was evaluated using FLuc-hMDR1-3' UTR obtained by the method described in the above-mentioned (1). MCF7-ADR cells (100 μl) prepared to 50000 cells/ml were seeded on a 96-well plate and incubated overnight at 37° C. The next day, FLuc-hRPN2-3' UTR (300 ng), *Renilla* luciferase expression vector (50 ng), and 2 μM Pre-miR™ miRNA27b Precursor Molecule (manufactured by Life Technologies) or Pre-miR™ miRNA Precursor Molecules-Negative Control (NC1) (manufactured by Life Technologies) (1 μl) were transfected to the aforementioned cells by using a Lipofectamine 2000 reagent (manufactured by Invitrogen). The cells were cultured in the presence of 5% $CO_2$ at 37° C. for 1 day, and the expression level of firefly and *Renilla* luciferase was measured by using Dual-Glo Luciferase Assay System (manufactured by Promega) and Envision 2101 Multilabel Reader (manufactured by PerkinElmer). As a result, the luciferase activity of the cells introduced with Pre-miR™ miRNA27b Precursor Molecule (manufactured by Life Technologies) was found to have decreased as compared to the cells introduced with a control, Pre-miR™ miRNA Precursor Molecules-Negative Control (NC1) (manufactured by Life Technologies) (FIG. 3). That is, miR27b was shown to suppress MDR1 expression.

Example 3

Figure 4:
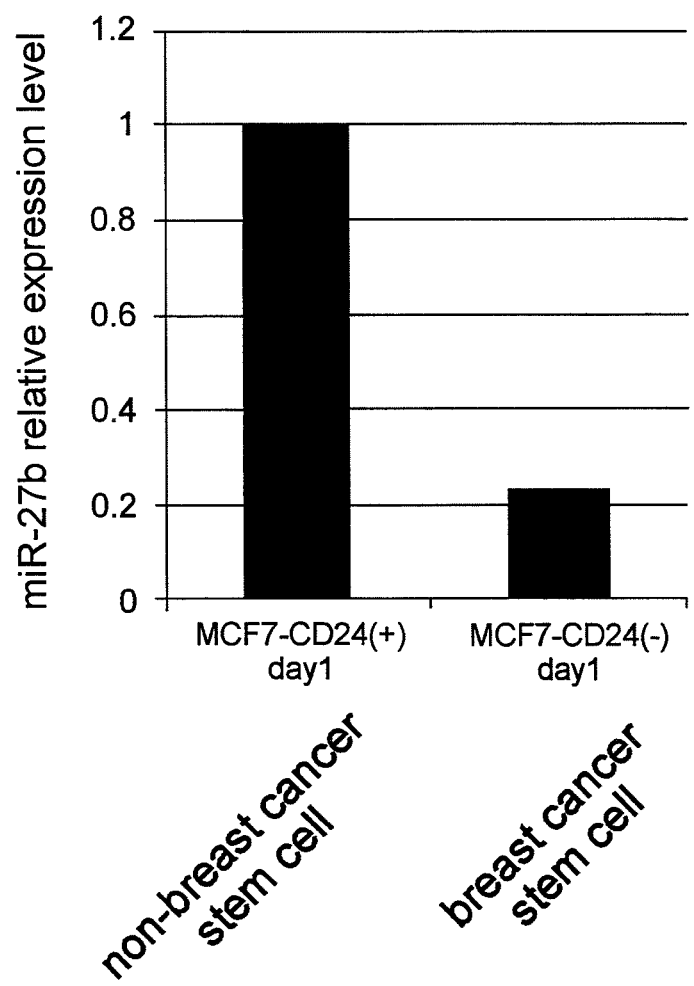
FIG. 4 shows the levels of miR27b expression in breast cancer cells and breast cancer stem cells.

Expression of miR27b in Breast Cancer Stem Cell $1 \times 10^6$ MCF7 cells and 10 μL CD24-PE antibody (manufactured by BD Biosciences) were incubated at 4° C. for 30 min. The cells were washed twice with PBS, and the cells were suspended in 500 μL of PBS containing 5 μL of 0.1 mg/mL Propidium iodide. The obtained cell suspension was applied to a cell sorter (manufactured by Bay Bioscience) to fractionate into a CD24 positive cell group (cancer cell group) and a CD24 negative cell group (cancer stem cell group). RNA was prepared from both cell fractions by using mirVana miRNA isolation kit (manufactured by Life Technologies), and the level of miR27b expression was quantified by the method described in Reference Example 1. As a result, it was found that the level of miR27b expression decreased in the CD24 negative cell group (cancer stem cell group) (FIG. 4).

Example 4

CD44 Expression-Suppressive Activity of miR27b (1) Construction of FLuc-hCD44-3' UTR A reaction mixture (20 μL) containing MCF7-ADR cell-derived cDNA library solution (2 μL), a primer consisting of a base sequence shown by SEQ ID NO: 9 (100 pmol), a primer consisting of a base sequence shown by SEQ ID NO: 10 (100 pmol), Taq polymerase (manufactured by Life Technologies) (0.1 μL), Taq polymerase-attached buffer (2 μL) and Taq polymerase-attached dNTP mixture (2 μL) was prepared. PCR was performed under the conditions of a treatment at 95° C. for 9 min, then 25 repeats of an incubation cycle at 95° C. for 30 sec, at 62° C. for 30 sec, and at 72° C. for 1 min, and lastly an incubation at 72° C. for 5 min. After PCR, an about 840 bp PCR product was recovered by agarose electrophoresis. The recovered PCR product was subcloned to XbaI site of pGL-3 vector (manufactured by Promega), and E. coli DH5α strain competent cell (manufactured by TOYOBO) was transformed with the plasmid. The transformed cells were cultivated in 50 μg/mL kanamycin-containing LB medium (100 ml), and the obtained cultivated bacteria were used for separation and purification using a QIAGEN Plasmid Maxi kit (manufactured by QIAGEN) to give plasmid FLuc-hCD44-3' UTR wherein 3' UTR region of human-derived RPN2 gene is linked to the 3' side of Firefly luciferase gene. Using the obtained plasmid as a template, BigDye (registered trade mark) Terminator v3.1 Cycle Sequencing kit (manufactured by Life Technologies) and ABI PRISM (registered trade mark) 3100 Genetic Analyzer sequence reader (manufactured by Life Technologies), the base sequence of 3' UTR region of human-derived CD44 gene consisting of the base sequence shown by SEQ ID NO: 11 was determined.

(2) Luciferase Assay

Figure 5:
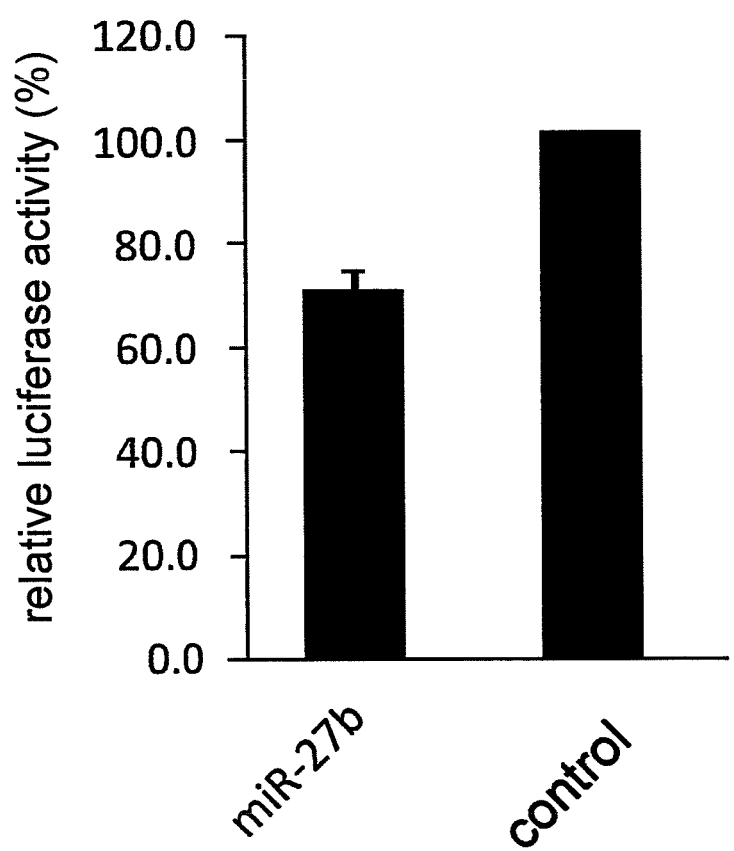
FIG. 5 shows suppression of CD44 expression by miR27b.

Then, CD44 expression suppressive activity of miR27b was evaluated using FLuc-hCD44-3' UTR obtained by the method described in the above-mentioned (1). MCF7-ADR cells (100 μl) prepared to 50000 cells/ml were seeded on a 96-well plate and incubated overnight at 37° C. The next day, FLuc-hRPN2-3' UTR (300 ng), Renilla luciferase expression vector (50 ng), and 2 μM pre-miR27b or NC1 (manufactured by Life Technologies) (1 μl) were transfected to the aforementioned cells by using a Lipofectamine 2000 reagent (manufactured by Invitrogen). The cells were cultured in the presence of 5% $CO_2$ at 37° C. for 1 day, and the expression level of firefly and Renilla luciferase was measured by using Dual-Glo Luciferase Assay System (manufactured by Promega) and Envision 2101 Multilabel Reader (manufactured by PerkinElmer). As a result, the luciferase activity of the cells introduced with Pre-miR™ miRNA27b Precursor Molecule (manufactured by Life Technologies) was found to have decreased as compared to the cells introduced with a control, Pre-miR™ miRNA Precursor Molecules-Negative Control (NC1) (manufactured by Life Technologies) (FIG. 5). That is, miR27b was shown to suppress CD44 expression.

Example 5

Cell Proliferation Activity of miR27b Constitutively Expressing MCF7-ADR-Luc Cell (1) Preparation of miR27b Expression Vector 10 nM Synthetic miR27b (4 μl) consisting of the base sequence shown by SEQ ID NO: 12 and pcDNA6.2-GW/EmGFP-miR (manufactured by Invitrogen) (10 ng) were mixed, and a ligation reaction was performed using a ligation kit (manufactured by Invitrogen) at room temperature for 5 min. After the reaction, the ligation reaction mixture (2 μL) and E. coli TOP10 strain competent cell (manufactured by Invitrogen) were used to give E. coli TOP10 transformed cells. The transformed cells were cultivated in 50 μg/mL spectinomycin-containing LB medium (100 mL), and the obtained cultivated bacteria were used for separation and purification using a QIAGEN Plasmid Maxi kit to give pcDNA6.2-GW/EmGFP-miR-miR27b, which is a miR27b expression vector.

(2) Preparation of miR27b Constitutively Expressing Cell pcDNA6.2-GW/EmGFP-miR-miR27b prepared by the aforementioned method was introduced into MCF7-ADR-luc cell by using a Lipofectamine 2000 reagent. The cells were continuously cultured in a medium containing 2 μg/mL Blastcidin for 14 days, and the surviving cells were isolated to give miR27b constitutively expressing cells. Separately, a cell introduced with pcDNA6.2-GW/EmGFP-miR was prepared by a similar method and used as a control cell in the subsequent experiment.

(3) Cell Proliferation Activity of miR27b Constitutively Expressing Cell

Figure 6:
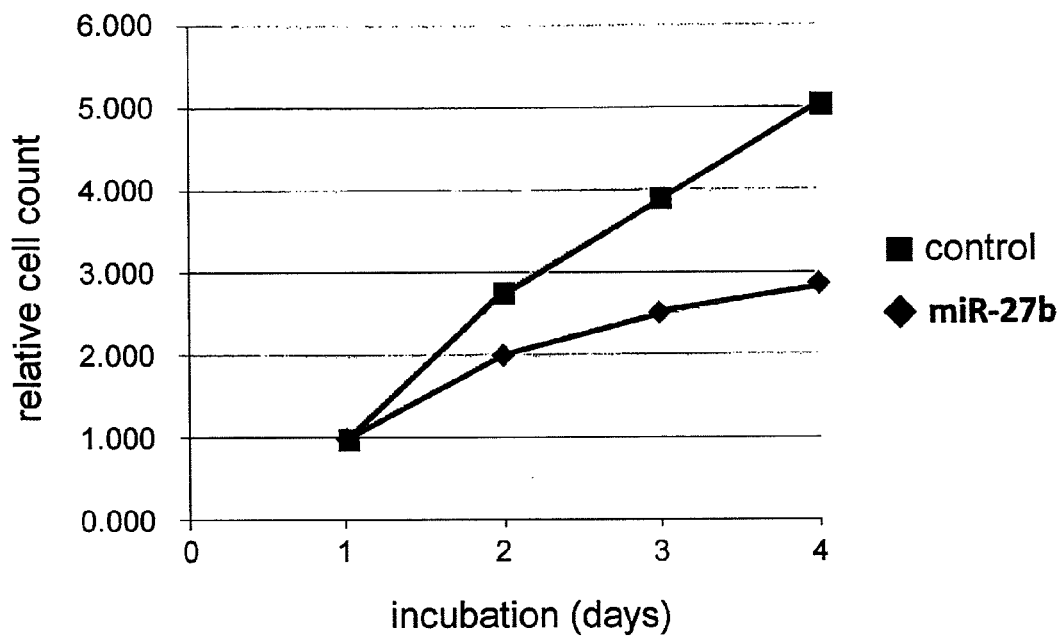
FIG. 6 shows cell proliferation of miR27b constitutively expressing MCF7-ADR-luc cells.

The miR27b constitutively expressing MCF7-ADR-luc cells and the control cells prepared to 10,000 cells/ml were seeded in a 96 well plate, and the cell proliferation activity was measured for 4 days using Tetracolor one for cell proliferation assay (manufactured by SEIKAGAKU CORPORATION). As a result, it was found that the cell proliferation rate of miR27b constitutively expressing cell was lower than that of the control cell (FIG. 6).

Example 6

Figure 7:
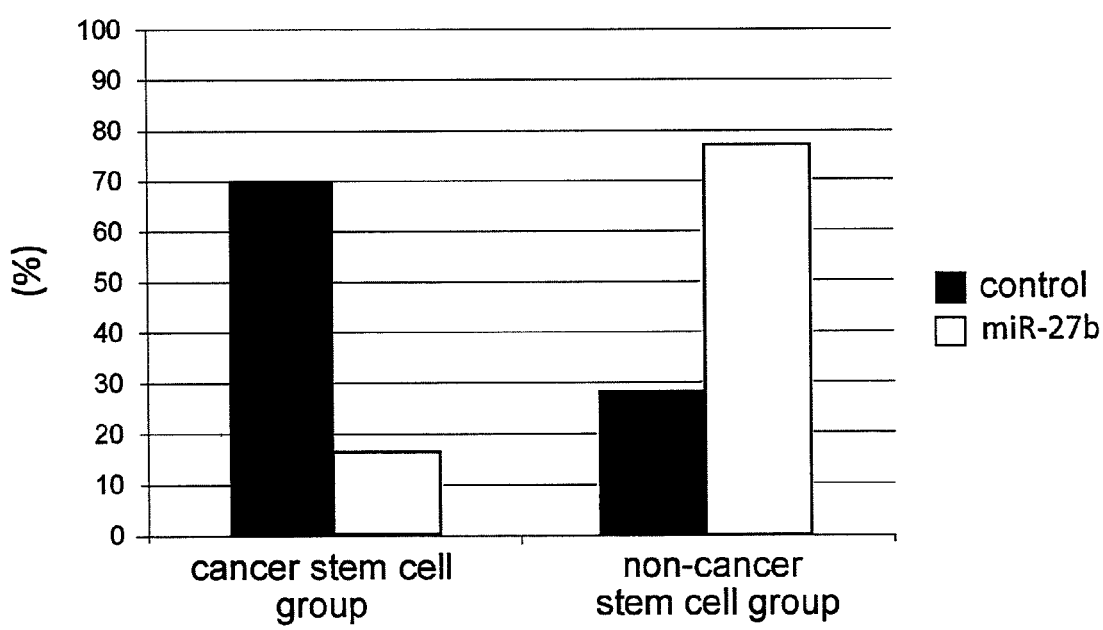
FIG. 7 shows ratios of a cancer stem cell group in miR27b constitutively expressing MCF7-ADR-luc cells.

Existence Ratio of Cancer Stem Cell in miR27b Constitutively Expressing MCF7-ADR-luc Cell $1 \times 10^6$ miR27b constitutively expressing MCF7-ADR-luc cells and the control cell were each incubated with 10 μL of CD24-PE antibody (manufactured by BD Biosciences) at 4° C. for 30 min. The cells were washed twice with PBS, and the cells were suspended in 500 μL of PBS containing 5 μL of 0.1 mg/mL Propidium iodide. The obtained cell suspensions were applied to a cell sorter (manufactured by Bay Bioscience), and the cell group positive to both GFP and CD24 (cancer cell group), and GFP positive, CD24 negative cell group (cancer stem cell group) were counted. As a result, it was found that the ratio of the cancer stem cell group in miR27b constitutively expressing MCF7-ADR-luc cells decreased as compared to the control cell but that of the non-cancer stem cell group increased (FIG. 7).

Example 7

Expression of miR27b in Drug Resistant PC14 Cell (PC14 Cell)

Figure 8:
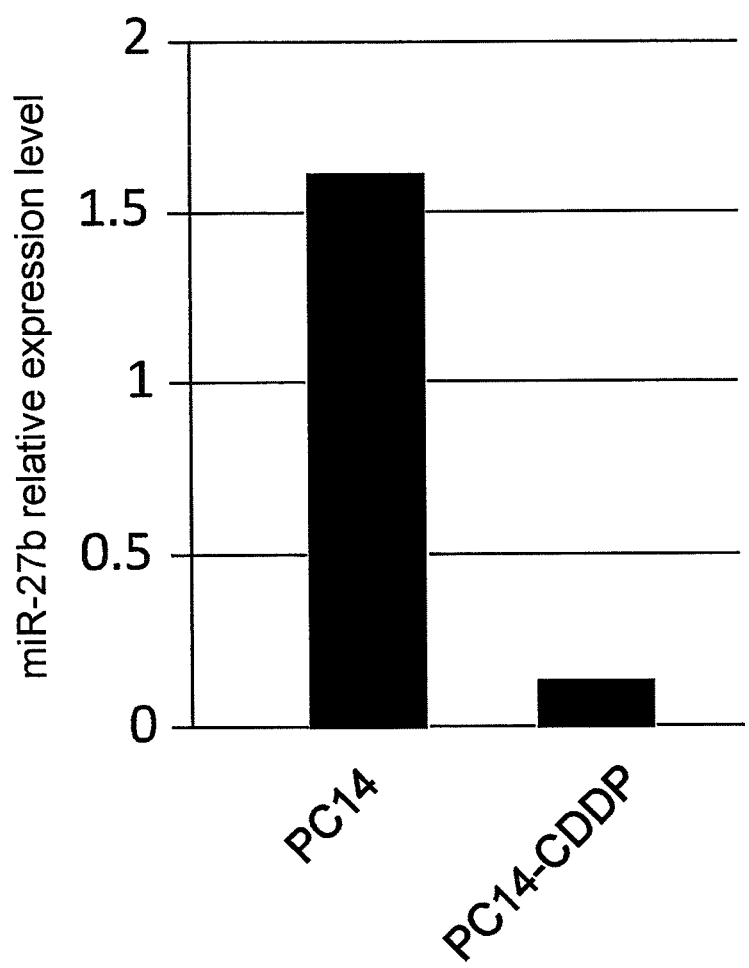
FIG. 8 shows levels of miR27b expression in PC14 cells

PC14 cell, which is a lung cancer cell line, and drug resistant lung cancer cell line PC14-CDDP cell were cultivated in DMEM medium supplemented with 10% fetal bovine serum (FBS), microRNAs were extracted from the both cell lines by using a mirVana RNA Isolation kit (manufactured by Life Technologies), according to the protocol attached to the kit. Using the obtained microRNA as a template, TaqMan MicroRNA Reverse Transcription kit (manufactured by Life Technologies), and miR27b TaqMan MicroRNA Assay or U6 TaqMan MicroRNA Assay (manufactured by Life Technologies), reverse transcription reaction was performed. That is, microRNA (5 μL), 100 mM dNTPs (with dTTP) (0.15 μL), MultiScribe Reverse Transcriptase (50 U/μL) (1 μL), 10× Reverse Transcription Buffer (1.5 μL), RNase Inhibitor (20 U/μL) (0.19 μL), Nuclease-free water (4.16 μL), and TaqMan MicroRNA Assay (5×) (3 μL) were mixed, and the mixture was incubated at 16° C. for 30 min, at 42° C. for 30 min, and at 85° C. for 5 min. A 15-fold diluted solution (1.33 μL) of the reaction mixture, TaqMan MicroRNA Assay (20×) (1 μL), TaqMan 2× Universal PCR Master Mix, No AmpErase UNGa (manufactured by Life Technologies) (10 μL), and Nuclease-free water (7.67 μL) were mixed and, after incubation at 95° C. for 10 min, a PCR reaction including 40 repeats of an incubation cycle at 95° C. for 15 sec, and at 60° C. for 1 min was performed using a 7300 Real Time PCR System (manufactured by Life Technologies) was performed and the expression levels of miR27b, U6 in MCF7, MCF7-ADR cells were quantified. As a result, as shown in FIG. 8, the level of miR27b expression in PC14-CDDP cell was found to have decreased as compared to PC14 cell.

Example 8

Tumor Forming Ability of miR27b Constitutively Expressing MCF7-ADR-luc Cell

The same number of miR27b constitutively expressing MCF7-ADR-luc cells and control cells are each transplanted near the mammary gland of a nude mouse. The luciferase luminescence level is measured by bioimaging every day after the transplantation. As a result, even though the same number of cells were transplanted, the luminescence level of miR27b constitutively expressing MCF7-ADR-luc cell is shown to have decreased as compared to the control cell. Thus, it is clear that a forced expression of miR27b decreases the tumor forming ability.

INDUSTRIAL APPLICABILITY

The therapeutic agent for tumor of the present invention is useful for the treatment or prophylaxis of a drug-resistant cancer, and a disease caused by cancer recurrence or tumor metastasis. The method of the present invention enables determination of a drug-resistant cancer and a cancer stem cell, and can provide a method of screening for an agent for determining a drug-resistant cancer or a cancer stem cell, a substance having an action to suppress growth of a drug-resistance, and a substance having an action to inhibit tumor metastasis.

This application is based on a patent application No. 2009-230016 filed in Japan (filing date: Oct. 1, 2009), the contents of which are incorporated in full herein.

The invention claimed is:

1. A method of treating breast cancer, comprising administering an effective amount of a nucleic acid comprising miR27b or a nucleotide sequence having 70% or more identity with the nucleotide sequence shown by SEQ ID NO: 1 and having a function equivalent to miR27b to a subject in need thereof, wherein said breast cancer shows a decreased expression level of miR27b as compared to normal breast tissue.

2. The method according to claim 1, wherein the nucleic acid is single stranded or double stranded.

3. The method according to claim 1, wherein the miR27b consists of the nucleotide sequence shown by SEQ ID NO: 1.

4. The method according to claim 1, wherein the nucleic acid is an RNA consisting of:
   the nucleotide sequence shown by SEQ ID NO: 1;
   a partial sequence of SEQ ID NO: 1 having a function equivalent to miR27b; or
   a modified product of SEQ ID NO: 1 having a function equivalent to miR27b.

5. The method according to claim 1, wherein the nucleic acid is an RNA consisting of the nucleotide sequence shown by SEQ ID NO: 1.

6. The method according to claim 1, wherein the nucleic acid comprising miR27b is at least one kind of nucleic acid selected from the group consisting of miR27b and a precursor thereof.

7. The method according to claim 6, wherein the precursor is pri-miRNA or pre-miRNA of miR27b.

8. The method according to claim 1, wherein the breast cancer is drug-resistant.

9. The method according to claim 1 for the suppression or prophylaxis of tumor metastasis.

10. The method according to claim 1 for the suppression or prophylaxis of cancer recurrence.

11. A method of treating breast cancer, comprising administering
   (A) a nucleic acid comprising miR27b or a nucleotide sequence having 70% identity or more with the nucleotide sequence shown by SEQ ID NO: 1 and having a function equivalent to miR27b, and
   (B) an antitumor agent
   in combination.

12. The method according to claim 11, wherein the breast cancer is drug-resistant.

13. A method of treating breast cancer, comprising administering a pharmaceutical composition comprising
   an effective amount of a nucleic acid comprising miR27b or a nucleotide sequence having 90% identity or more with the nucleotide sequence shown by SEQ ID NO: 1 and having a function equivalent to miR27b, and
   a pharmaceutically acceptable carrier,
   to a mammal having or at recognized risk of having breast cancer.

* * * * *

UNITED STATES PATENT AND TRADEMARK OFFICE
CERTIFICATE OF CORRECTION

PATENT NO.         : 8,921,333 B2
APPLICATION NO.    : 13/498771
DATED              : December 30, 2014
INVENTOR(S)        : T. Ochiya et al.

It is certified that error appears in the above-identified patent and that said Letters Patent is hereby corrected as shown below:

On the title page, the second Assignee listed in column 1 item (73), change "Asahi Pharma Corporation" to -- Asahi Kasei Pharma Corporation --.

Signed and Sealed this
Twenty-sixth Day of May, 2015

Michelle K. Lee
*Director of the United States Patent and Trademark Office*

```
SEQUENCE LISTING

<160> NUMBER OF SEQ ID NOS: 12

<210> SEQ ID NO 1
<211> LENGTH: 21
<212> TYPE: RNA
<213> ORGANISM: Homo sapiens

<400> SEQUENCE: 1
uucacagugg cuaaguucug c                                              21

<210> SEQ ID NO 2
<211> LENGTH: 97
<212> TYPE: RNA
<213> ORGANISM: Homo sapiens

<400> SEQUENCE: 2
accucucuaa caaggugcag agcuuagcug auuggugaac agugauuggu uuccgcuuug    60
uucacagugg cuaaguucug caccugaaga gaaggug                             97

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctagtctaga ttccagaaga aagatggaaa                                     30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 4
ctagtctaga ctattgttac cctctttatt                                    30

<210> SEQ ID NO 5
<211> LENGTH: 301
<212> TYPE: DNA
<213> ORGANISM: Homo sapiens

<400> SEQUENCE: 5
ttccagaaga aagatggaaa ttctgaaaac tgaatgtcaa gaaaggagt caagaacaat    60 tcacagtatg agaagaaaaa tggaaaaaaa aaactttatt taaaaagaa aaagtccag   120 attgtagtta acttttgct tgttttcag tttccccaac acacagcaga tacctggtga    180
gctcagatag tctctttctc tgacactgtg taagaagctg tgaatattcc taacttaccc  240
agatgttgct tttgaaaagt tgaaatgtgt aattgttttg gaataaagag ggtaacaata  300
g                                                                 301

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctagtctaga gatgttaaat acttttta                                      28

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctagtctaga aatgcaagaa tcag                                          24

<210> SEQ ID NO 8
<211> LENGTH: 589
<212> TYPE: DNA
<213> ORGANISM: Homo sapiens

<400> SEQUENCE: 8
gatgttaaat acttttaat atttgtttag atatgacatt tattcaaagt taaaagcaaa    60
cacttacaga attatgaaga ggtatctgtt taacatttcc tcagtcaagt tcagagtctt  120
cagagacttc gtaattaaag gaacagagtg agagacatca tcaagtggag agaaatcata  180
gtttaaactg cattataaat tttataacag aattaaagta gattttaaaa gataaaatgt  240
gtaattttgt ttatatttc ccatttggac tgtaactgac tgccttgcta aaagattata   300
gaagtagcaa aaagtattga aatgtttgca taaagtgtct ataataaaac taaactttca  360
tgtgactgga gtcatcttgt ccaaactgcc tgtaatata tcttctctca attggaatat   420
tgtagataac ttctgcttta aaaagttttt ctttaaatat acctactcat ttttgtggga  480
atggttaagc agtttaaata attcctgttg tatatgtcta ttcacattgg gtcttacaga  540
accatctggc ttcattcttc ttggacttga tcctgctgat tcttgcatt               589

```
<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaatctagat ggccacctgt tctctcctgt                                        30

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttttctagag gtaccaatgg atctggccaa tgatgttcac aga                         43

<210> SEQ ID NO 11
<211> LENGTH: 846
<212> TYPE: DNA
<213> ORGANISM: Homo sapiens

<400> SEQUENCE: 11
tggccacctg ttctctcctg tgaaaggctt tgcaaagtca cattaagttt gcatgacctg       60
ttatccctgg ggccctattt catagaggct ggccctatta gtgatttcca aaaacaatat      120
ggaagtgcct tttgatgtct tacaataaga gaagaagcca atggaaatga agagattgg       180 caaaggggaa ggatgatgcc atgtagatcc tgtttgacat ttttatggct gtatttgtaa     240
acttaaacac accagtgtct gttcttgatg cagttgctat ttaggatgag ttaagtgcct      300
ggggagtccc tcaaaaggtt aaagggattc ccatcattgg aatcttatca ccagataggc      360
aagtttatga ccaaacaaga gagtactggc tttatcctct aacctcatat tttctcccac      420
ttggcaagtc ctttgtggca tttattcatc agtcagggtg tccgattggt cctagaactt      480
ccaaaggctg cttgtcatag aagccattgc atctataaag caacggctcc tgttaaatgg     540
tatctccttt ctgaggctcc tactaaaagt catttgttac ctaaacttat gtgcttaaca     600
ggcaatgctt ctcagaccac aaagcagaaa gaagaagaaa agctcctgac taaatcaggg      660
ctgggcttag acagagttga tctgtagaat atctttaaag gagagatgtc aactttctgc      720
actattccca gcctctgctc ctccctgtct accctctccc ctccctctct ccctccactt      780
caccccacaa tcttgaaaaa cttcctttct cttctgtgaa catcattggc cagatccatt      840
ggtacc                                                                 846

<210> SEQ ID NO 12
<211> LENGTH: 66
<212> TYPE: DNA
<213> ORGANISM: Artificial Sequence
<220> FEATURE:
<223> OTHER INFORMATION: Description of Artificial Sequence: Synthetic
      miR27b coding oligonucleotide

<400> SEQUENCE: 12
tgctgttcac agtggctaag ttctgcgttt tggccactga ctgacgcaga acttagccac       60
tgtgaa                                                                  66
```